United States Patent [19]

Ozawa et al.

[11] 4,215,138
[45] Jul. 29, 1980

[54] INSECTICIDAL COMPOUNDS OF PHENYLCYCLOPROPANE CARBOXYLIC ACID ESTERS

[75] Inventors: Kiyomi Ozawa; Shigeru Ishii, both of Funabashi; Mamoru Hayashi, Shiraoka; Masayoshi Hirose, Shiraoka; Ryoichi Nonaka, Shiraoka, all of Japan

[73] Assignee: Nissan Chemical Industries, Ltd., Tokyo, Japan

[21] Appl. No.: 969,866

[22] Filed: Dec. 15, 1978

[30] Foreign Application Priority Data

Dec. 27, 1977 [JP] Japan ................................. 52/156381
Apr. 3, 1978 [JP] Japan ................................. 53/38968

[51] Int. Cl.$^2$ ........................ A01N 9/28; A01N 9/06; C07D 317/44; C07C 121/64
[52] U.S. Cl. ........................... 424/282; 260/340.5 R; 260/465 D; 424/304
[58] Field of Search .................... 260/340.5 R, 465 D; 424/282, 304

[56] References Cited

U.S. PATENT DOCUMENTS

| | | | |
|---|---|---|---|
| 3,835,176 | 9/1974 | Matsuo et al. | 260/465 D |
| 3,979,424 | 9/1976 | Searle et al. | 260/465 D X |
| 4,031,239 | 6/1977 | Shrider | 424/304 |
| 4,060,632 | 11/1977 | Addor | 424/304 |
| 4,061,664 | 12/1977 | Wood | 260/465 D |
| 4,083,863 | 4/1978 | Brand | 260/465 D |
| 4,091,010 | 5/1978 | Norton | 260/465 D |
| 4,096,170 | 6/1978 | Van den Brink et al. | 260/465 D |
| 4,105,780 | 8/1978 | Berkelhammer et al. | 260/340.5 R |
| 4,137,324 | 1/1979 | Elliott et al. | 424/282 |
| 4,157,397 | 6/1979 | Engel | 424/282 X |
| 4,160,842 | 7/1979 | Engel | 424/282 X |

*Primary Examiner*—Ethel G. Love
*Attorney, Agent, or Firm*—Oblon, Fisher, Spivak, McClelland & Maier

[57] ABSTRACT

Insecticidal compounds having the formula

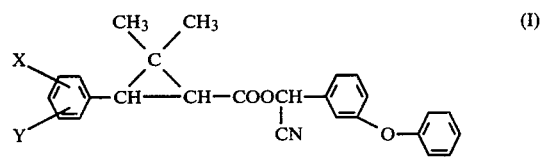

wherein X and Y are the same or different and represent a hydrogen or a halogen atom, methyl group, a lower alkoxy group, trifluoromethyl group, phenoxy group or X and Y form

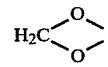

group except both of X and Y are hydrogen atoms.

7 Claims, No Drawings

INSECTICIDAL COMPOUNDS OF PHENYLCYCLOPROPANE CARBOXYLIC ACID ESTERS

BACKGROUND OF THE INVENTION

1. Field of the Invention

The present invention relates to novel compounds of substituted phenylcyclopropane carboxylic acid esters which have excellent insecticidal activity to various insects injurious to sanitation as well as agriculture, horticulture and forest. 2 Description of the Prior Arts Recently, structure modifications of natural pyrethrin have been widely studied and various cyclopropane carboxylic acid ester derivatives have been used as insecticides.

The present invention is to provide novel insecticidal compounds having superior insecticidal activity to those of the conventional pyrethroids.

The inventors have studied on structural modifications of pyrethroids and have found that the novel substituted phenylcyclopropane carboxylic acid esters have strong insecticidal effect and wide insecticidal spectrum and are substantially non-toxic to fishes and shell-fishes.

Heretofore, certain phenylcyclopropane carboxylic acid derivatives have been known.

The compounds having the formula

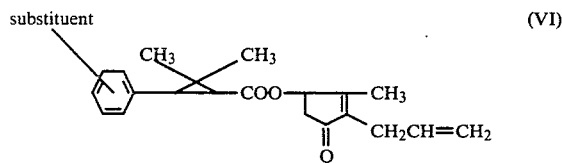

have been known in Collection of Czechoslovak Chemical Communication 24 2460 (1959) and 25 1815 (1960).

These compounds are carboxylic acid esters having

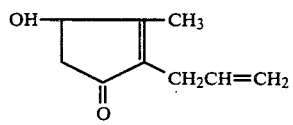

as the alcohol moiety. However, insecticidal activity of the compounds for houseflies is only similar to that of allethrin of one of the commerciallized pyrethroids when the substituent on the phenyl group is a hydrogen atom and the insecticidal activity is inferior when the substituent on the phenyl group is chlorine, or fluorine atom or methyl or methoxy group.

The compounds having the formula

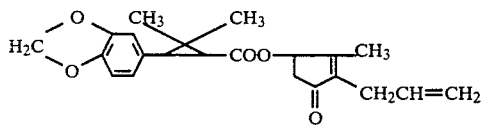

has been disclosed in Bochu Kagaku Vol. 27, III, page 51. However, the insecticidal activity of the compound is only similar to that of allethrin.

The inventors have checked a phenylcyclopropane carboxylic acid ester illustrated below.

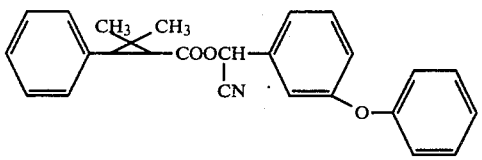

This compound has no substituent on phenyl group. However, an insecticidal activity of this compound is quite low.

On the other hand, the substituted phenyl cyclopropane carboxylic acid esters of this invention possess high insecticidal effects as described later in this invention.

It is important to obtain an insecticidal compound having highly insecticidal effects and widely used for controlling insects injurious to sanitation as well as agriculture, horticulture and forest.

SUMMARY OF THE INVENTION

It is an object of the present invention to provide novel insecticidal compounds which have high insecticidal effects and low toxicity to mammals and fishes.

Another object of the present invention is to provide a new use of novel insecticidal compounds of substituted phenylcyclopropane carboxylic acid esters.

The other objects of the present invention is to provide a process for producing the insecticidal compound of substituted phenylcyclopropane carboxylic acid ester.

Briefly, the foregoing and other objects of the present invention have been attained by providing insecticidal compounds of phenylcyclopropane carboxylic acid esters having the formula

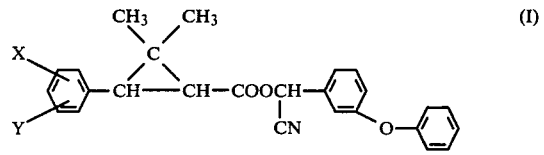

wherein X and Y are the same or different and represent a hydrogen or a halogen atom, methyl group, a lower alkoxy group, trifluoromethyl group, phenoxy group or X and Y form

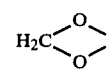

group except both of X and Y are hydrogen atoms.

DETAILED DESCRIPTION OF THE PREFERRED EMBODIMENTS

The novel insecticidal compounds of substituted phenylcyclopropane carboxylic acid esters having the formula (I) have excellent insecticidal effects, because of the substituent on phenyl group. The insecticidal activity of the insecticidal compounds of the present invention is significantly superior to that of allethrin as one of the commerciallized pyrethroids.

It has been well-known that pyrethrins and synthetic pyrethroids have high toxicity to fishes and shell-fishes (TLM: less than 0.1 ppm to Killifish). On the contrary, TLM in 48 hours for the insecticidal compounds of the present invention are approximately 50 ppm to Killifish.

It is an unexpected result from the conventional knowledge that the insecticidal compounds of the present invention have excellent insecticidal activity and significant low toxicity to fishes.

The process for producing the novel insecticidal compounds will be illustrated by the following schemes.

In the schemes (A) to (D), the references X and Y are defined above and Z represents a halogen atom or sulfonate group and Hal represent a halogen atom.

In the process (B), the starting components are reacted in an inert solvent such as acetonitrile in the prsence of a dehydrating agent such as dicyclohexylcarbodiimide. Alternatively, p-toluene-sulfonic acid or conc. sulfuric acid used in an esterification can be used as the catalyst.

In the process (C), the starting materials are reacted in a solvent such as dimethylformamide, preferably under refluxing. In the course of the reaction, an alkali metal or alkaline earth metal hydroxide is used for converting an acid to a salt such as potassium or sodium salt etc.

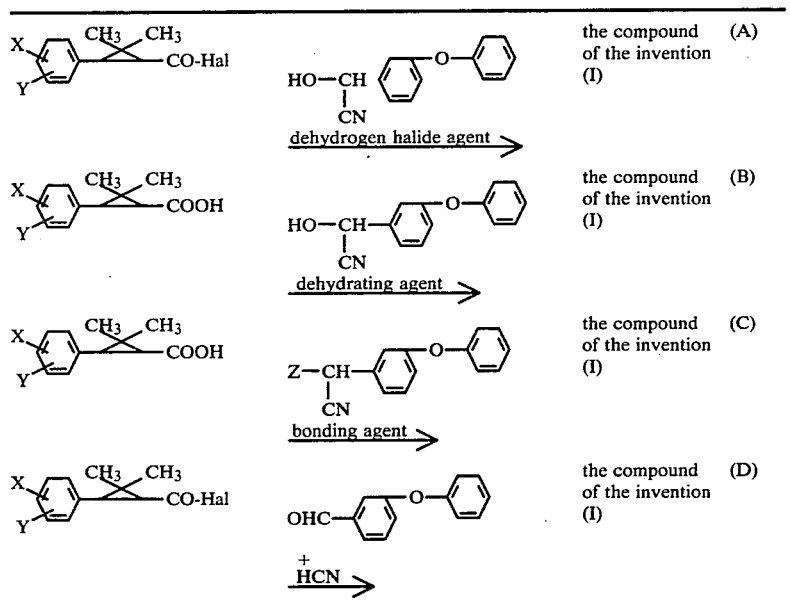

The insecticidal compounds of the present invention can be obtained in high yield by the processes of (A) to (D).

The processes are further illustrated in detail as follows.

In the process (A), an organic tertiary base such as pyridine and triethylamine or an inorganic base such as alkali metal or alkaline earth metal hydroxides is used as the dehydrogen halide agent and the starting materials are reacted in an inert solvent such as benzene.

In the process (D), the starting materials are reacted in an aprotic solvent which is not miscible to water such as n-heptane in the presence of water soluble cyan compound such as sodium cyanate and a phase transfer catalyst such as tetra-n-butyl ammonium chloride or methyl tri-2-methyl-phenylammonium chloride to obtain the insecticidal compound of the present invention in high yield.

Typical compounds of the present invention will be shown in the following list.

| Compound No. | Structure | Refractive index($n_D^{20}$) |
|---|---|---|
| 1 | CH$_3$—⟨⟩—C(CH$_3$)(CH$_3$)—COOCH(CN)—⟨⟩—O—⟨⟩ | 1.5840 |
| 2 | CH$_3$O—⟨⟩—C(CH$_3$)(CH$_3$)—COOCH(CN)—⟨⟩—O—⟨⟩ | 1.5687 |
| 3 | C$_2$H$_5$O—⟨⟩—C(CH$_3$)(CH$_3$)—COOCH(CN)—⟨⟩—O—⟨⟩ | 1.5770 |
| 4 | CH$_3$O—⟨⟩—C(CH$_3$)(CH$_3$)—COOCH(CN)—⟨⟩—O—⟨⟩ | 1.5700 |

-continued

| Compound No. | Structure | Refractive index($n_D^{20}$) |
|---|---|---|
| 5 | Cl-C6H3-C(CH3)(CH3)-COOCH(CN)-C6H4-O-C6H5 | 1.5805 |
| 6 | Cl,Cl-C6H3-C(CH3)(CH3)-COOCH(CN)-C6H4-O-C6H5 | 1.5762 |
| 7 | F3C-C6H4-C(CH3)(CH3)-COOCH(CN)-C6H4-O-C6H5 | 1.5461 |
| 8 | C6H5-O-C6H4-C(CH3)(CH3)-COOCH(CN)-C6H4-O-C6H5 | 1.5865 |
| 9 | CH3-C6H4-C(CH3)(CH3)-COOCH(CN)-C6H4-O-C6H5 | 1.5692 |
| 10 | CF3-C6H4-C(CH3)(CH3)-COOCH(CN)-C6H4-O-C6H5 | 1.5452 |
| 11 | CH3,Cl-C6H3-C(CH3)(CH3)-COOCH(CN)-C6H4-O-C6H5 | 1.5300 |
| 12 | CH3,F-C6H3-C(CH3)(CH3)-COOCH(CN)-C6H4-O-C6H5 | 1.5722 |
| 13 | F-C6H4-C(CH3)(CH3)-COOCH(CN)-C6H4-O-C6H5 | 1.5620 |
| 14 | Br-C6H4-C(CH3)(CH3)-COOCH(CN)-C6H4-O-C6H5 | 1.5581 |
| 15 | Cl-C6H4-C(CH3)(CH3)-COOCH(CN)-C6H4-O-C6H5 | 1.5801 |
| 16 | O-CH2-O-C6H3-C(CH3)(CH3)-COOCH(CN)-C6H4-O-C6H5 | 1.5835 |

The optical isomers of esters based on each asymmetric carbon atom in each carboxylic acid moiety or each alcohol moiety are also included in the compounds of the present invention.

Certain examples of syntheses of the compounds of the present invention will be illustrated below.

PREPARATION 1

Preparation of Compound No. 1

Into 20 ml of benzene, 2.3 g of α-cyano-m-phenoxybenzyl alcohol and 0.8 g of pyridine were dissolved. The solution was stirred under cooling with ice and 2.2 g of trans-2,2-dimethyl-3-(p-methylphenyl)-cyclopropane carboxylic acid chloride was added dropwise to the solution. After reacting them for 1 hour, the product was washed twice with 10 ml of water and the organic layer was dried over anhydrous sodium sulfate and benzene was distilled off under a reduced pressure. The residual oily product was purified by a column chromatography (alumina: developing solvent benzene) giving 3.8 g of the object compound ($n_D^{20}$: 1.5840).

NMR spectrum; δ. ppm C Cl4; 0.89(3H, S); 1.27 (1.5H, S); 1.38(1.5H, S); 1.90(1H, d, J=6.0 Hz); 2.26(3H, S); 2.67(1H, d, J=6.0 Hz); 6.27(0.5H, S); 6.36(0.5H, S); 6.80 to 7.40(13H, m).

PREPARATION 2

Preparation of Compound No. 1

A mixture of 4 g of m-phenoxybenzaldehyde, 4.5 g of trans-2,2-dimethyl-3-(p-methylphenyl)-cyclopropane carboxylic acid chloride, 1.2 g of sodium cyanate, 3.0 ml of water, 0.3 g of tetra-n-butylammonium chloride and 40 ml of n-heptane were vigorously stirred at room temperature to react them for 40 hours. After reacting them, the resulting precipitate was filtered off and the filtrate was washed with an aqueous solution of sodium bicarbonate, with an aqueous solution of sodium hydrogen sulfite and with water and the organic layer was dried over anhydrous sodium sulfate and n-heptane was distilled off under a reduced pressure from the organic layer giving the object compound as a crude ester. The product was purified by a silica gel chromatography (n-hexane: ethyl acetate=4:1) giving 6.5 g of the object compound.

The NMR spectrum of the compound was the same with that of Preparation 1.

PREPARATION 3

Preparation of Compound No. 15

Into 20 ml of benzene, 2.3 g of α-cyano-m-phenoxybenzyl alcohol and 0.8 g of pyridine were dissolved. The solution was stirred under cooling with ice and 2.4 g of trans-2,2-dimethyl-3-(p-chlorophenyl)-cyclopropane carboxylic acid chloride was added dropwise to the solution. The crude product, obtained according to the procedure similar to that of Preparation 1, was purified by a column chromatography (alumina; developing solvent; benzene) giving 4 g of the object compound. ($n_D^{20}$: 1.5801)

NMR spectrum; δ, ppm, C Cl$_4$; 0.88(3H, m); 1.27(1.5H, S); 1.38(1.5H, S); 1.82(1H, d, J=6.0 H$_z$); 2.65(1H, d, J=6.0 H$_z$); 6.31(0.5H, S); 6.36(0.5H, S); 6.80 to 7.50(13H, m).

PREPARATION 4

Preparation of Compound No. 16

A mixture of 4 g of m-phenoxybenzaldehyde, 5.1 g of trans-2,2-dimethyl-3-(3',4'-methylenedioxyphenyl)-cyclopropane carboxylic acid chloride, 1.2 g of sodium cyanate, 3.0 ml of water, 0.3 g of tetra-n-butylammonium chloride and 40 ml of n-heptane was vigorously stirred at room temperature to react them for 40 hours. The crude product, obtained according to the procedure similar to that of Preparation 2, was purified by a silica gel column chromatography (n-hexane; ethyl acetate=4:1) giving 7.5 g of the object compound in a pure form ($n_D^{20}$: 1.5835).

NMR spectrum; δ, ppm, C Cl$_4$; 0.92(3H, bs); 1.25(1.5H bs); 1.37(1.5H bs); 1.87(1H, d, J=6.0 H$_z$); 2.62(1H, d, J=6.0 H$_z$); 5.79(2H, s); 6.32(1H, m); 6.40 to 7.60(12H, m).

PREPARATION 5

Preparation of Compound No. 10

Into 20 ml of benzene, 2.3 g of α-cyano-m-phenoxybenzyl alcohol and 0.8 g of pyridine were dissolved. The solution was stirred under cooling with ice and 2.8 g of trans-2,2-dimethyl-3-(p-trifluoromethylphenyl)-cyclopropane carboxylic acid chloride was added dropwise to the solution. The crude product, obtained according to the procedure similar to that of Preparation 1, was purified by a column chromatography (alumina; developing solvent benzene) giving 4.5 g of the object compound ($n_D^{20}$: 1.5452).

NMR spectrum; δ, ppm, C Cl$_4$; 0.89 (3H, m); 1.30 (1.5H, S); 1.40 (1.5H, S); 2.03 (1H, d, J=6.0 H$_z$); 2.72 (1H, d, J=6.0 H$_z$); 6.30 (0.5H, S); 6.37 (0.5H, S); 6.80 to 7.60 (13H, m).

The insecticidal compounds of substituted phenylcyclopropane carboxylic acid esters having the formula (I) are useful as insecticides for controlling insects injurious to sanitation as well as agriculture, horticulture and forest, for example, the following injurious insects:

Insects injurious to sanitation: house fly and pale house mosquito;

Insects injurious to agriculture, horticulture and forest:

Rice: rice stem borer, smaller brown planthopper, white-backed planthopper, brown planthopper and green rice leafhopper;

Vegetables: cabbage army worm, tobacco cutworm, common white, green peach aphid, diamondback moth and 28-spotted lady beetle;

Fruits: smaller tea tortorix, comstock mealybug, european red mite, citrus red mite and two spotted spider mite;

Cotton: beat armyworm, boll weevil, pink bollworm, cotton aphid;

The injurious insects to which the insectidical compound of the present invention is applied, are not limited to the above-mentioned insects.

The insecticidal activity of the compounds (I) is imparted not only young larva but also old larva in direct or in penetration.

When the insecticidal compound is used as an insecticidal composition, suitable adjuvant is admixed with the insecticidal compound at suitable ratio to dissolve, to disperse, to suspend, to blend, to immerse, to adsorb or to adhere the insecticidal compound so as to form suitable composition in a form of a solution, a dispersion, an emulsion, an oil spray, a wettable powder, a dust, a granule, a pellet, a paste or an aerosol.

The insecticidal composition incorporating the compound of the present invention as an active ingredient can be blended to suitable other agricultural composition, such as insecticides, acaricides, fungicides, fertilizers, plant nutritions and plant growth regulators which is applied in the same manner.

The insecticidal effect of the compound of the present invention can be improved by combining it with synergist such as piperonyl butoxide (P.B.) octachlorodipropyl ether or N-octyl bicycloheptene dicarboxyimide.

The stability of the compound of the present invention can be improved by combining an antioxident such as phenol type antioxidants e.g. 2,6-di-t-butyl-4-methylphenol (B.H.T.) and 2,6-di-t-butylphenol and amine type antioxidants.

Certain insecticidal compositions containing the compound of the present invention will be illustrated as follows.

| COMPOSITION 1. Emulsifiable concentrate: | |
|---|---|
| Compound No. 1 | 25 wt. parts |
| Xylol | 30 wt. parts |
| Sorphol 2680 (Toho Chem.) | 15 wt. parts |
| Dimethylformamide | 30 wt. parts |

The components were uniformly mixed and diluted 50 times with the quantity of water and the aqueous solution was sprayed in amounts of 25 to 50 ml/m$^2$ or it was diluted with 1,000 to 2,000 times the quantity of water and the aqueous solution was sprayed in amounts of 100 to 400 liter/10 ares.

| COMPOSITION 2: Oil spray: | |
|---|---|
| Compound No. 1 | 0.2 wt. parts |
| Piperonyl butoxide | 0.8 wt. parts |
| Kerosene | 99.0 wt. parts |

The components were uniformly mixed to obtain an oily solution.

The oil spray was applied in amounts of 25 to 50 ml/m² to a drain or a puddle.

| COMPOSITION 3 Dust: | |
|---|---|
| Compound No. 2 | 0.4 wt. parts |
| Piperonyl butoxide | 1.6 wt. parts |
| Talc. | 98 wt. parts |

The components were uniformly mixed to obtain a dust.

The dust was applied at a ratio of 15 g/m² or 3 to 4 Kg/10 area.

The similar compositions were prepared by substituting the active ingredient to the other compounds of the invention and were applied by the same manners.

The following is certain experiments which were conducted with the compositions of the present invention.

As references, the following active ingredients were used instead of the compound of the present invention.

Reference Compound A

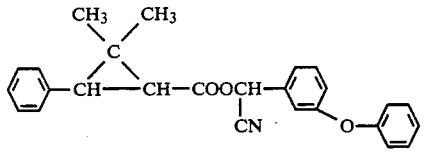

Resmethrin

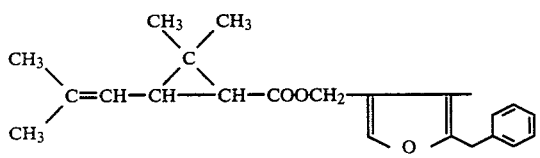

Allethrin

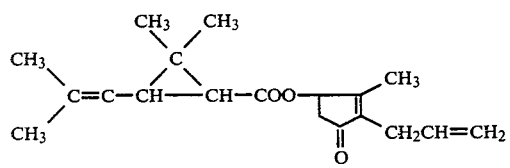

PAP

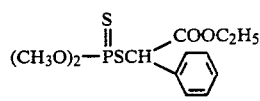

EXPERIMENTS 1

Contact test for killing houseflies

A 1 cc quantity of 10 ppm and 1 ppm solution of each of the insecticidal compounds of the present invention and the references in acetone was dropped onto the bottom of a Petri dish, and was spread uniformly over the surface of the disk. Acetone was completely evaporated at room temperature. Ten adult houseflies were placed in the dish, which was covered with a plastic cover having many holes. The Petri dish was maintained in a constant temperature room at 25° C. for 24 hours and percent mortality of the houseflies was determined.

The test was repeated twice and the results are shown in Table 1.

Table 1

| Active ingredient | Concentration | Percent mortality (%) | |
|---|---|---|---|
| | | 10 ppm | 1 ppm |
| Compound No. 1 | | 100 | 100 |
| Compound No. 2 | | 100 | 100 |
| Compound No. 3 | | 100 | 55 |
| Compound No. 4 | | 100 | 70 |
| Compound No. 5 | | 100 | 60 |
| Compound No. 7 | | 100 | 50 |
| Compound No. 12 | | 100 | 60 |
| Compound No. 15 | | 100 | 85 |
| Compound No. 16 | | 100 | 55 |
| Reference Compound A | | 100 | 5 |
| Reference Resmethrin | | 100 | 30 |
| Reference PAP | | 100 | 0 |

EXPERIMENTS 2

Test for killing houseflies (topical application)

The compound of the present invention or its mixture with piperonylbutoxide (1:4) or a reference compound was dissolved in acetone. Each acetone solution was applied dropwise on each thoracic tergum of houseflies by a microcylinder.

The treated houseflies and water wet absorbent cotton were put in a polystyrene cup having a diameter of 9 cm and a height of 6 cm and the polystyrene cup was maintained in a constant temperature room at 25° C. for 24 hours and number of mortalities of the houseflies was observed and median lethal dose (LD$_{50}$) was calculated by Finny's graphic method.

The tests were carried out in two groups wherein 10 houseflies were used in each group. The results are shown in Table 2.

Table 2

| Active ingredient | LD$_{50}$ (μg/fly) |
|---|---|
| Compound No. 1 | 0.05 |
| Compound No. 15 | 0.17 |
| Compound No. 1 + PB | 0.03 |
| Compound No. 15 + PB | 0.09 |
| Compound No. 2 | 0.28 |
| Reference | |
| Compound A | 0.38 |
| Allethrin | 0.90 |
| PAP | 0.06 |

EXPERIMENT 3

Contact test for killing green rice leafhopper

Stems and leaves of a rice seedling were dipped in each emulsion of each of the composition of the compounds of the invention (concentration shown in Table) for 10 seconds and were dried in air. The stems and leaves were covered with a glass cylinder and 15 of adults green rice leafhoppers were released into the cylinder which was covered with a cover having holes and was maintained in a constant temperature room at 25° C. for 24 hours or 48 hours and percent mortality was determined. The test was repeated two times. The results are shown in Table 3.

Table 3

| Active ingredient | Concent-ration | Percent mortality (%) | | | |
|---|---|---|---|---|---|
| | | 100 ppm | | 10 ppm | |
| | | after 24 hr. | after 48 hr. | after 24 hr. | after 48 hr. |
| Compound No. 1 | | 60 | 100 | 20 | 65 |

EXPERIMENT 4

Contact test for killing Tobacco cutworm

Leaves of cabbage were dipped in 100 ppm aqueous emulsion of the compound of the invention or the reference for 10 seconds. The leaves were taken up and dried in air and put in a Petri dish having a diameter of 7.5 cm. Ten of tobacco cutworm (third instar) were put in the Petri dish which was covered with a cover having many holes. The Petri dish was maintained in a constant temperature room at 25° C. for 48 hours and percent mortality was determined. The tests were carried out in two groups. As the results percent mortalities were more than 70% when the compounds of the pressent invention were respectively applied.

However, percent mortality was zero when the Reference compound A was applied and percent mortality was 10% when 10 ppm. PAP was applied whereas percent mortality was 40% when 10 ppm compound No. 15 was applied and it was 100% when 100 ppm Compound No. 15 was applied.

EXPERIMENT 5

Test for killing rice stem borer

The compound of the present invention or a reference compound was dissolved in acetone. Each acetone solution was applied dropwise on each thoracic tergum of rice stem borers.

The treated rice stem borers and water wet filter paper and rice stem were put in a Petri dish having a diameter of 9 cm. The Petri dish was maintained in a constant temperature room at 25° C. for 48 hours and number of mortalities of rice stem borers was observed and median lethal dose ($LD_{50}$) was calculated by Finny's graphic method.

The tests were carried out in two groups wherein 10 rice stem borers were used in each group. The results are shown in Table 4.

Table 4

| Active ingredient | $LD_{50}$ (μg/borer( |
|---|---|
| Compound No. 15 | 0.16 |
| Reference Compound A | 0.30 |
| Resmethrin | 0.31 |

Table 4-continued

| Active ingredient | $LD_{50}$ (μg/borer( |
|---|---|
| PAP | 0.19 |

EXPERIMENT 6

Test for killing Green peach aphid

Each emulsion of the compound of the present invention or the reference (concentration shown in Table) was prepared. Ten of green peach aphid were inoculated on leaves of cabbage in a Petri dish having a diameter of 3 cm and 2 ml of each emulsion was sprayed and it was covered and the Petri dish was maintained in a constant temperture room at 25° C. for 24 hours or 48 hours and percent mortality of green peach aphids in the Petri dish was determined. The tests were carried out in two groups. The results are shown in Table 5.

Table 5

| Active ingredient | Concent-ration (ppm) | Percent mortality (%) | |
|---|---|---|---|
| | | after 24 hr. | after 48 hr. |
| Compound No. 10 | 100 | 100 | 100 |
| Reference Dimethoate | 100 | 95 | 100 |
| Non-treated | — | 0 | 0 |

EXPERIMENT 7

Test for killing 28-spotted lady beetle

A piece of potato was dipped in an emulsion of the compound of the invention or the reference compound (concentration shown in Table) and it was taken up and dried in air and was put in a Petri dish. Ten of lavea of 28-spotted lady beetle (second instar) were put in each Petri dish and it was covered with a cover having many holes, and the Petri dish was maintained in a constant temperature room at 25° C. for 24 hours, 48 hours or 120 hours and percent mortailty was determined. The tests were carried out in two groups. The results are shown in Table 6.

Table 6

| Active ingredient | Concent-ration ppm | Percent mortality (%) | | |
|---|---|---|---|---|
| | | after 24 hr. | after 48 hr. | after 120 hr. |
| Compound No. 10 | 100 | 95 | 95 | 100 |
| | 10 | 5 | 25 | 90 |
| Reference PAP | 100 | 30 | 90 | 95 |
| | 10 | 0 | 0 | 5 |
| Non-treated | — | 5 | 5 | 10 | what is claimed is:

1. An insecticidal compound of phenylcyclopropane carboxylic acid ester having the formula

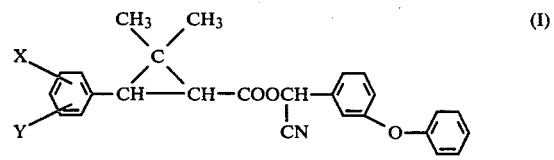

(I)

wherein X and Y are the same or different and represent a hydrogen or a halogen atom, methyl group, a lower alkoxy group, trifluoromethyl group, phenoxy group or X and Y form

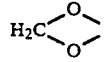

group; with the proviso, that X and Y are not both hydrogen atoms.

2. An insecticidal compound of phenylcyclopropane carboxylic acid ester having the formula

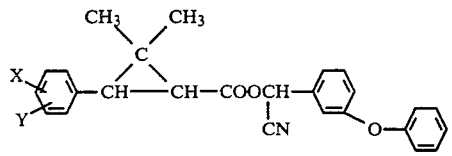

wherein X and Y are the same or different and represent a hydrogen or a halogen atom; methyl group, a lower alkoxy group, trifluoromethyl group or phenoxy group; with the proviso, that X and Y are not both hydrogen atoms.

3. An insecticidal compound of phenylcyclopropane carboxylic acid ester having the formula

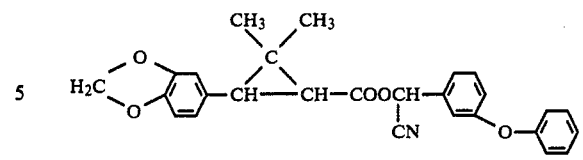

4. An insecticidal compound of phenylcyclopropane carboxylic acid ester having the formula

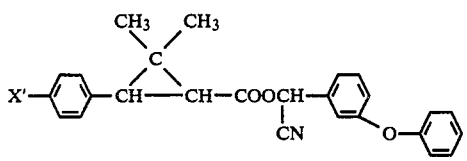

wherein X' represents $CH_3-$, $CF_3-$ or $Cl-$.

5. An insecticidal composition which comprises an insecticidally effective amount of a compound of phenylcyclopropane carboxylic acid ester having the formula (I), according to claim 1, and an adjuvant in a form of a solution, a dispersion, an emulsion, an oil spray, a wettable powder, a dust, a granule, a tablet, a pellet, a paste or an aerosol.

6. An insecticidal composition according to claim 5 which comprises said insecticidal compound of phenylcyclopropane carboxylic acid ester having the formula (I) and a synergist of piperonyl butoxide, octachlorodipropyl ether or N-octyl bicycloheptane dicarboxyimide.

7. An insecticidal composition according to claim 5 which comprises said insecticidal compound of phenylcyclopropane carboxylic acid ester having the formula (I) and an antioxidant.

* * * * *